(12) United States Patent
Burkett

(10) Patent No.: US 7,659,057 B2
(45) Date of Patent: *Feb. 9, 2010

(54) STAIN-DIRECTED MOLECULAR ANALYSIS FOR CANCER PROGNOSIS AND DIAGNOSIS

(75) Inventor: Douglas D. Burkett, Gilbert, AZ (US)

(73) Assignee: Zila Biotechnology, Inc., Scottsdale, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 10/484,420

(22) PCT Filed: Oct. 5, 2002

(86) PCT No.: PCT/US02/32067

§ 371 (c)(1),
(2), (4) Date: Jun. 16, 2004

(87) PCT Pub. No.: WO03/072826

PCT Pub. Date: Sep. 4, 2003

(65) Prior Publication Data

US 2004/0235067 A1    Nov. 25, 2004

Related U.S. Application Data

(60) Continuation-in-part of application No. PCT/US00/26551, filed on Sep. 26, 2000, and a division of application No. 10/017,007, filed on Dec. 14, 2001, now abandoned, and a continuation-in-part of application No. 10/758,936, filed on Jan. 14, 2004, now abandoned.

(51) Int. Cl.
C12Q 1/68 (2006.01)
(52) U.S. Cl. .......................................................... 435/6
(58) Field of Classification Search ...................... 435/6
See application file for complete search history.

(56) References Cited

U.S. PATENT DOCUMENTS

| | | | |
|---|---|---|---|
| 4,321,251 A * | 3/1982 | Mashberg | 424/9.7 |
| 5,372,801 A | 12/1994 | Malmros et al. | |
| 5,882,627 A | 3/1999 | Pomerantz | |
| 5,981,293 A | 11/1999 | Charlton et al. | |
| 6,086,852 A | 7/2000 | Burkett | |
| 6,194,573 B1 | 2/2001 | Burkett | |
| 6,241,689 B1 | 6/2001 | Chard et al. | |
| 6,256,530 B1 | 7/2001 | Wolfe | |
| 6,372,904 B2 | 4/2002 | Burkett | |
| 6,376,525 B1 | 4/2002 | Kong | |
| 6,405,070 B1 | 6/2002 | Banerjee | |
| 6,417,003 B1 | 7/2002 | Cipriani | |
| 6,649,144 B1 | 11/2003 | Burkett et al. | |

FOREIGN PATENT DOCUMENTS

| | | | |
|---|---|---|---|
| WO | 94/19492 | 9/1994 | |
| WO | WO 01/64110 A1 * | 7/2001 | |
| WO | 02/26266 | 4/2002 | |
| WO | 03/057918 | 7/2003 | |

OTHER PUBLICATIONS

Handler, Janice, Diagnostic and Management of Oral Soft-Tissue Lesions: The ise of Biopsy, Toluidine Blue staining, and Brush biopsy, Aug. 2001 issue, apges 1-9.*
Berger, Abi. Saliva Test Could diagnose Cancer. BMJ, vol. 320, p. 825, Mar. 2000.*
Fliss et al. Facile Detection of Mitochondrial DNA mutations in Tumors and bodily fluids. Science, vol. 287, pp. 2017-2019, Mar. 2000.*
Mashberg et al. A Cancer Journal for Clinicians. vol. 45, No. 6, pp. 328-351, Nov.-Dec. 1995.*
Rosin et al. Clinical Cancer Research. vol. 6, pp. 357-362, Feb. 2000.*
Guo et al., Allelic Losses in OraTest-directed Biopsies of Patients with Prior Upper Aerodigestive Tract Malignancy, Clinical Cancer Research, Jul. 2001, vol. 7, 1963-1968.
Zhi-Ping et al., Benign Clonal Keratinocyte Patches with p53 Mutations Show No Genetic Link to Synchronous Squamous Cell Precancer or Cancer in Human Skin, American Journal of Pathology, May 1997, vol. 150, No. 5, pp. 1791-1803.
Spafford et al., Detection of Head and Neck Squamous Cell Carcinoma among Exfoliated Oral Mucosal Cells by Microsatellite Analysis, Clinical Cancer Research, Mar. 2001, vol. 7, pp. 607-612.
Mashberg, Final evaluation of tolonium chloride rinse for screening of high-risk patients with asymptomatic squamous carcinoma, JADA, Mar. 1983, vol. 106, pp. 319-323.
Mao et al., Frequent microsatellite alterations at chromosomes 9p21 and 3p14 in oral premalignant lesions and their value in cancer risk assessment, Nature Medicine, Jun. 1996, vol. 2, No. 6, pp. 682-685.
El-Naggar et al., Genetic Heterogeneity in Saliva from Patients with Oral Squamous Carcinomas, Journal of Molecular Diagnosis, Nov. 2001, vol. 3, No. 4, pp. 164-170
Rosas et al., Promoter Hypermethylation Patterns of p16, O6-Methylguanine-DNA-methyltranferase, and Death-associated Protein Kinase in Tumors and Saliva of Head and Neck Cancer Patients, Cancer Research, Feb. 2001, vol. 61, pp. 939-942.
Martin et al., The application of toluidine blue as a diagnostic adjunct in the detection of epithelial dysplasia, Oral Surgery Oral Medicine Oral Pathology, Apr. 1998, vol. 85, No. 4, pp. 444-446.
Reddy et al., Toluidine Blue Staining of Oral Cancer and Precancerous Lesions, Indian J Med Res, Aug. 1973, vol. 61, No. 8, pp. 1161-1164.
Contini et al., Vital staining of oesophagus in patients with head and neck cancer: still a worthwhile procedure, Ital J Gastroeterol, 1991, vol. 23, pp. 5-8.

* cited by examiner

Primary Examiner—Gary Benzion
Assistant Examiner—Cynthia B Wilder
(74) Attorney, Agent, or Firm—Jeffer Mangels Butler & Marmaro LLP

(57) ABSTRACT

The location at which tissue samples are obtained to determine whether cells exhibit characeristics associated with cell differentiation or cancer by molecular analysis is determined by topically applying to epithelial tissue a dye that selectively stains cancer and precancerous tissue.

11 Claims, No Drawings

STAIN-DIRECTED MOLECULAR ANALYSIS FOR CANCER PROGNOSIS AND DIAGNOSIS

This application is a Continuation-In-Part of Then-Copending International Patent Application No. PCT/US00/26551, filed 26 Sep. 2000 (U.S. application Ser. No. 10/111,545, now abandoned), is a Division of U.S. patent application Ser. No. 10/017,007, filed Dec. 14, 2001, now abandoned) and a Continuation-In-Part of U.S. patent application Ser. No. 10/758,936, filed Jan. 14, 2004 now abandoned.

This invention relates to a combined method for the early location and prognosis of tissue containing potentially invasive cancer cells, before the normal visual appearance of the tissue indicates potential development of invasive cancer, thus delaying a diagnosis of such tissue as precancerous or cancerous by conventional location, excision and histological procedures.

In another respect, the invention relates to a combined method for location and detection of tissue containing such potentially invasive cancer cells, the normal visual appearance of which is anomalous, which may lead to delay in obtaining a diagnosis indicating treatment.

BACKGROUND OF THE INVENTION

Patients who delay in obtaining a cancer consultation for at least two months have significantly higher relative hazards of death than do patients with a shorter delay. (See Cancer, 92[11]:2885-2891, 2001). Thus, if patients are more regularly subjected cancer screening, coupled with a definitive procedure for making an early prognosis or diagnosis, the mortality rate risks of cancer would be reduced.

Accordingly, I provide prognostic and diagnostic methods for early prediction of eventual development of invasive cancer or for definitive diagnosis, which are stepwise, rapid, conclusive, and readily adaptable as a clinical protocol.

Development of Pre-Cancerous & Cancerous Tissue:

The development of tumors requires two separate mutational events. One of these events may occur in the germline and be inherited. The second then occurs somatically. Alternatively, the two mutational events may occur only in the somatic cell of an individual.

Cancer Screening Procedures

Conventional Visual Cancer Screening

Cellular mutations which are normally visible are well documented and may involve thickening, discoloration, atypical moles, or hardening. Several tissue features for differentiating early melanomas from benign melanocytic nevi are known to those skilled in the art. For example:

| Feature | Benign Mole | Melanoma |
| --- | --- | --- |
| Asymmetry | No | Yes |
| Border Integrity | No | Yes |
| Color | Uniform, tan/brown | Variegated, black |
| Diameter | <6 mm | May be >6 mm |

However, these normally visible features and their characteristics may not be apparent until the tissue involved is advanced on the normal progression pathway of cancer. Consequently, a simple, rapid and relatively accurate screening method was needed to enable the clinician to locate suspect tissue before the normally visible characteristics of cancerous or precancerous tissue appear.

In Vivo Cancer Screening Procedures for Early Location of Potentially Cancerous Tissue In vivo screening technique has now been developed to quickly and noninvasively identify gross or specific anatomical locations of a patient's body are likely to contain cells with the tumor or cancerous phenotype at stages before conventional visual observation of the tissue would reveal such suspect tissue. These in vivo screening techniques to locate such potentially cancerous sites, particularly epithelial cancers, are fast and quite feasible, even for the general clinical practitioner.

Gross Anatomical Screening:

One example of gross anatomical screening is the Polymerase Chain Reaction (PCR) analysis of a simple saliva sample. Saliva contains exfoliated cells that originate from the head and neck region—a large surface area—that is a common origin of cancer cells, especially in patients who expose these areas to nicotine, alcohol, and other known or suspected carcinogens. PCR analysis serves as a gross preliminary screening procedure, which determines whether exfoliated cells found in a patient's saliva exhibit a cancerous phenotype, indicating the development of cancer within this gross anatomical area. For example, see Spafford, M. F., et al, "Detection of Head and Neck Squamous Cell Carcinoma Among Exfoliated Mucosal Cells by Microsatellite Analysis", *Clin. Cancer Res.* 2001, Mar. 7(3):607-612.

Specific Location Screening by Selective In Vivo Dye Staining

Selective in vivo tissue-staining techniques known in the art employ toluidine blue O (TBO) dye and other cationic supravital marking agents to selectively locate cancerous and precancerous tissue. U.S. Pat. No. 4,321,251 to Mashberg and in the U.S. Pat. No. 5,372,801 to Tucci et al. provide general descriptions of a staining dye protocol named after Mashberg (the Mashberg protocol).

Advancements in TBO staining techniques for detecting and locating cancer and precancer are disclosed in U.S. Pat. Nos. 6,086,852 and 6,194,573 to Burkett. Burkett disclosed processes for synthesyzing TBO products and processes for manufacturing TBO with improved yield and improved methods for the detection of dysplastic tissue. Other dyes which are effective for in vivo cancer location are disclosed in U.S. Pat. No. 5,882,627 to Pomerantz and include the dyes, Azure A, Azure B, Azure C, and certain other oxazine and thiazine dyes.

Prognosis and Diagnosis Based on Molecular Analysis

Mutations generally result from intramolecular gene reorganization, such as a substitution, addition, or deletion of a nucleotide, the subunit of DNA and RNA, respectively. Recently, however, genetic mapping has developed ways to detect mutations of nucleotides characteristic of cancer and precancer, such as the methylation patterns of DNA and RNA, and enzymatic activity, which is a direct consequence of alterations of the nucleotide sequence or the "genetic code". It has also been determined that cancerous activity can be detected by changes in the mitochondria.

I. Genetic Mutations

DNA Analysis

Analysis of DNA polymorphisms reveals a significant difference between normal cells and tumor cells: whereas normal cells are heterozygous at many loci, the tumors are homozygous at the same loci (loss of heterozygosity).

Tumor suppressor genes are often associated with the loss of one chromosome or a part of a chromosome, resulting in a reduction to homozygosity, through elimination of one allele of a tumor suppressor gene as well as surrounding markers. The remaining tumor suppressor allele is inactivated by either an inherited or a somatic mutation. Some examples of well documented tumor suppression genes include: Adenomatous polyposis of the colon gene (APC), Familial breast/ovarian cancer genes 1 and 2 (BRCA1 and BRCA2), Cadherin 1 (epithelial cadherin or E-cadherin) gene (CDH1), Multiple endocrine neoplasia type 1 gene (MEN1), Neurofibromatosis type 1 gene (NF1), Protein kinase A type 1, alpha, regulatory subunit gene (PRKAR1 A), Retinoblastoma gene (RB1), Serine/threonine kinase 11 gene (STK11), and von Hipple-Lindau syndrome gene (VHL). Thus, critical chromosome loci are predictors of the probable onset of invasive cancer.

An example of DNA analysis includes Microsatellite Analysis for determining mutations or the instability of "chromosomal arms" or "microsatellites". Microsatellites are short repetitive sequences of DNA that have been observed to contain nucleotide mispairs, misalignments, or nucleotide slippage (looping or shortening). Mutations, such as these, are termed microsatellite instability and have become associated with a number of epithelial cancers.

More recent studies have identified new microsatellite markers for detecting loss of heterogeniety, before a cell undergoes abnormal morphological change. See Guo, Z., et al, "Allelic Losses in Ora Test-directed Biopsies of Patients with Prior Upper Aerodigestive Tract Malignancy", Clinical Canc. Res. Vol. 7, 1963-1968, July 2001.

Those skilled in the art understand that there are distinct differences, at the histologic level, at the genetic level and at the anatomic level in terms of right side/left side, between tumors with chromosomal instability and microsatellite instability. It is also known that in leukemias and lymphomas, major interstitial deletions and translocations occur at the gross chromosomal level. In various epithelial tumors such as, the changes occur differently, as major chromosomal arms have been shown to be lost. Tumors apparently progress down one pathway or the other but not both. (Oncology News International, Vol. 9, No. 8, Suppl. 2, August 2000) MSI analyses generally requires the use of five MS markers—two mononucleotide repeats and three dinucleotide repeats.

RNA Analysis

It is now possible to detect one somatic mutant mRNA molecule in a background of 1000 wild type mRNA molecules. This technique measures gene expression levels in samples containing as few as 10-20 cells, together with the capability for detection of somatic point mutations at several loci known to be altered with high frequency. Thus, it is possible to observe microheterogeneity in gene expression profiles in small clusters of cells in dysplasia and cancer.

Sequence detection was accomplished on oligonucleotide microarrays, using a target-directed DNA ligation step coupled to a Rolling Circle Amplification (RCA) unimolecular detection system. The DNA ligation step is adaptable to the detection of mRNAs containing point mutations. Lizardi, P. M., "Messenger RNA Profiling by Single Molecule Counting", Yale University, (2000), http://otir.cancer.gov/tech/imat_awards.html, (Nov. 28, 2001).

Telomeric DNA and Associative Protein, Telomerase

Telomeres are the DNA sequences, which are the specialized complexes at the ends of chromosomes. Telomerase, the ribonucleoprotein that helps maintain telomeres, is inactive in many adult human cell types, but is highly activated in most human cancers. It has been determined that a disruption or mutation in either the telomeric DNA or telomerase, or the intermediary RNA, can uncap the telomere, causing further damage to the DNA. Thus, it is known that a molecular analysis can detect either abnormal telomeric nucleotides or abnormal enzymatic activity of telomerase, which are equally associated with the proliferation of pre-cancerous cells. See, e.g., Kim, M. M., et al., "A Low Threshold Level of Expression of Mutant-template Telomerase RNA Inhibits Human Tumor Cell Proliferation", Proc. Natl. Acad. Sci. USA: Vol. 98, No. 14, 7982-7987, (July 2001).

II. Epigenetic Mutations

Aberrant promoter methylation was recently discovered to be a fundamental molecular abnormality leading to transcriptional silencing of tumor suppressor genes, DNA repair genes and metastasis inhibitor genes, and is linked to the predisposition of genetic alterations of other cancer-associated genes.

Somatic epigenetic alterations in DNA methylation are tightly linked to development, cell differentiation and neoplastic transformation. For instance, hypermethylation of CpG islands in promoter regions has been increasingly associated with transcriptional inactivation of tumor suppressor genes in carcinogenesis. Although techniques to measure methylation in specific DNA segments or in total DNA have been available, Yamamoto developed a method called "Methylation Sensitive-Amplified Fragment Length Polymorphism" (MS-AFLP) for identifying changes in methylation in the entire genome. This polymerase chain reaction (PCR)-based unbiased DNA fingerprinting technique permits the identification of the cleavage sites that exhibit DNA methylation alterations and subsequently allows the isolation of DNA fragments with these sites at their ends. Decreases or increases of band intensity, or differences in banding pattern, were specifically linked with the tumor phenotype.

Thus, methylation alteration provides identification of epigenetic alterations associated with cell differentiation and cancer. DNA mutation or loss of heterogeneity can be alternatively detected by measuring DNA methylation. See Yamamoto, F., Ph.D., "Technology to Detect Genome-wide DNA Methylation Changes", Burnham Institute, http://otir.cancer.gov/tech/imat_awards.html, (Nov. 28, 2001).

III. Mitochondrial Mutations

More recently, another cancer detection method was developed, based on the finding that mitochondrial DNA (mtDNA) exhibits mutations when derived from human cancerous cells.

There are an estimated 1000 different proteins in the mitochondria. Defects in such proteins can be characterized as "metabolic diseases", causing defects in transport mechanisms and ion channels, most notably, defects in the electron transport chain and oxidative phosphorylation. Nuclear mutations can affect mtDNA replication and repair, transcription, protein synthesis in the matrix, protein import, and other properties of the mitochondria. See, e.g., Fliss, et al., "Facile Detection of Mitochondrial DNA Mutations in Tumors and Bodily Fluids", Science 287, 2017-2019, (2000). In this study, DNA was extracted from autopsy-derived brain samples from 14 individuals, ranging in age from 23 to 93 years and tested for the three mutations by PNA-directed PCR clamping. The ability to detect very low levels of point mutations in mtDNA by PNA-directed PCR clamping, permitted analysis of the presence or absence of, e.g., the A8344G, A3253G and T414G, point mutations in tissues from individuals of varying ages. Lung cancer cases corresponded with mutant mtDNA bands, that were detected using a sensitive oligonucleotide-mismatch ligation assay and gel electrophoresis.

Thus, mutations within the mitochondrial genome are still another method for detecting cancerous activity in human cells. See also Parrella, P., et al., "Detection of Mitochondrial DNA Mutations in Primary Breast Cancer and Fine-Needle Aspirates", Cancer Res. 61, 7623-7626, (October, 2001). Advantageously, abnormal chromosomal expression, associated with cancer, can be detected with common molecular analysis at very early stages of pathogenic expression and with a very few number of affected cells.

However, given the expanse of the human body's cellular tissue that could possibly propagate invasive cancer tissue, diagnostic techniques such as genetic, epigenetic, or mitochondrial molecular analysis are not effective early cancer detection methods, because the effectiveness of these techniques directly depend on obtaining tissue samples from the specific tissue sites containing cells which are propagating cancer. Moreover, although some of the prior art screening methods are capable of identifying specific sites of suspect cancerous and precancerous tissue, the location and identification of such suspect tissue was, heretofore, generally followed by conventional histological examination of the suspect tissue such as lighted microscopy. Often, such conventional histological examination indicated that some of the locations identified by prior art techniques were not cancerous or precancerous, when, in fact, cells from these locations exhibited the markers for eventual development of cancer at that location, markers which could have been identified by molecular analysis, i.e., genetic code, (DNA or RNA), epi-genetic patterns, or mitochondrial DNA (mtDNA), characteristic of cancer cell propagation.

For example, subsequent application of molecular analysis techniques to cells derived from suspect tissue samples located by mitochondrial dye staining—cells that were originally determined by conventional histology to be "false positives" of the Mashberg protocol—revealed that a high proportion of these cells in fact contained markers that were the earliest indication of the eventual development of cancer at those suspect sites. (See Example II, below.)

BRIEF STATEMENT OF THE INVENTION

I have now discovered an improved prognostic and diagnostic method for detecting pre-cancerous and cancerous growth in human tissue which combines the advantages of prior art general or specific "location screening" technologies with the precise prognostic and diagnostic" technologies of cellular molecular analysis.

Briefly, my method comprises various combinations and subcombinations of up to three steps: (1) conducting a screening test that subjects saliva to polymerase chain reaction (PCR) analysis to determine whether head or neck cancer in this gross anatomical region is probable; (2) topically applying a stain in vivo, which selectively stains cancerous or precancerous tissue, to a gross anatomical region for visualization of the specific location of suspect cells, to enable cell extraction or a biopsy of the cells in such specific suspect location; and (3) subjecting cells obtained from such suspect location to molecular analysis, to determine whether said extracted cells exhibit characteristics associated with cell differentiation or cancer.

According to one embodiment of the invention, in vivo topical selective dye-staining of a gross anatomical location, to locate suspect tissues is combined with molecular analysis cells from the thus-located suspect tissue.

Yet another embodiment of the invention includes conducting a saliva screening test of head and neck tissues, followed by selective dye staining of said tissues to locate specific sites of suspect tissue, followed by molecular analysis of cells from such specific suspect sites to confirm whether the specifically identified suspect tissue contains cells which exhibit characteristics associated with cancer or the eventual development of cancer.

"Molecular Analysis"

As used herein, the term "molecular analysis" means a procedure for identifying cellular abnormalities which indicate cancer or the probable eventual development of cancer. Illustratively, these procedures include those which identify such abnormalities in the genetic code, i.e. DNA or RNA, in epi-genetic patterns, or in mitochondrial DNA (mtDNA), of suspect cells. Thus, although countless nucleotides within and exterior to a cell's nucleus can be observed to detect mutations, the term "molecular analysis" is limited to those procedures which determine whether a tumor phenotype is present in the suspect cells. Accordingly, target nucleotides or associated proteins and patterns, as well as the various other detection techniques known to one skilled in the art, are to be considered within the scope of the term "molecular analysis."

While the saliva screening test, Step 1, is specific to detecting only head and neck cancers, Steps 2-3 can be applied to any cells capable of visual inspection in vivo, including topical or internal tissues that may be observed within an internal cavity of the body or individual cells distributed within plasma fluid. Such combination of steps provides a simple clinical protocol that can identify the locations of precancerous, as well as suspect sites, well before onset of otherwise visible indications.

DETAILED DESCRIPTION OF THE INVENTION

My method comprises sequentially examining cells to first locate and identify tissue having suspect cells and then to examine cells from such suspect tissue to detect the presence of a cancerous or tumor phenotype. Tumor phenotypes include any mutation, e.g. allelic loss, loss of heterogeneity, mutation of tumor suppressor genes, abnormal DNA methylation, or abnormal mtDNA, associated with cancer.

The following detailed description of these sequential steps are provided to enable those skilled in the art to practice the invention and to indicate the presently preferred embodiments thereof. This description is not to be understood as limiting the scope of the invention, which is limited only by the appended claims.

Step 1: Saliva Screening for Head and Neck Cancer

Saliva samples can be collected in a number of ways. It is most important that the collection apparatus complies with the requirements of polymerase chain reaction (PCR) analysis and that the integrity of nucleic acids is not destroyed before analysis.

The PCR analysis detect an increase or decrease in short repetitive sequences, called microsatellite DNA. The microsatellite DNA correspond to an allele because of their location on the DNA. Mutations in microsatellite DNA are found to be most common in epithelial cancer phenotypes, and so is a particularly appropriate analysis of exfoliated cells found in saliva. A thorough description of this analysis is provided by U.S. Pat. No. 6,291,163, to Sidransky, incorporated herein by reference.

PCR analysis has become somewhat automated, as is described in U.S. Pat. No. 6,326,147, incorporated herein by reference. PCR is considered a method for nucleic acid amplification which allows for DNA and RNA sequencing with a minute amount of nucleic acid sequence. Two U.S. Pat. Nos. 5,981,293 and 6,241,689, describe apparatus suitable for collecting saliva samples.

Even though a patient may be found to positively exhibit signs of a cancerous phenotype upon saliva screening, the location of the cancer cells must then be identified before proper prognosis and treatment can be effected. Alternatively, even though a patient's saliva screen results in negative, meaning no cancer indications, the patient should still undergo a thorough visual examination (described in Step 2: Cellular Staining Location) for common and recurring cancer types.

Step 2: Cellular Staining Location

Step 2 enables a practitioner to precisely locate and select suspect cells in vivo, for later in vitro molecular analysis, providing the clinician with a prolonged view of the suspect site, enabling the practitioner to precisely select suspect cells among potentially numerous abnormal sites for molecular analysis during a biopsy procedure.

The presently preferred embodiment of the invention employs the in vivo Mashberg Protocol as it is improved and described in detail in U.S. Pat. No. 6,086,852, the contents of which are herein incorporated by reference in their entirety.

The protocol employs toluidine blue O (TBO) dye to selectively stain cancerous and precancerous tissue. The original diagnostic screening test was described in the U.S. Pat. No. 4,321,251 to Mashberg and in the U.S. Pat. No. 5,372,801 to Tucci et al., incorporated herein by reference.

Other cationic dyes, e.g. Azure B, Azure C and Brilliant Cresyl Blue, have been identified as useful for selectively marking cancerous and precancerous cells. See, for example, U.S. Pat. No. 5,882,672, to Pomerantz, incorporated here by reference.

If the staining technique indicates the presence of cancerous or precancerous tissue, surgical excision biopsy of the suspect tissue is performed and a subsequent molecular analysis, herein described in "Step3: Molecular Analysis Diagnosis-Prognosis" follows, to yield a prognosis/diagnosis of cancer or eventual development of cancer, if the molecular analysis determines that cells from the abnormal tissue are malignant or precancerous.

Step 3: Molecular Analysis Diagnosis-Prognosis

Cell samples for molecular analysis are derived from a variety of biopsy techniques, which, in general terms, involve the removal of a small piece of suspect tissue for molecular analysis. The method of tissue removal or extraction varies with the various types of biopsies. For example, the biopsy sample can comprise portions or skin lesions or isolated blood cells, e.g., erythrocytes, leukocytes, and lymphocytes, parathyroid tissue; salivary gland tissue; nasal mucosal tissue, oropharynx tissue, open lung tissue, small bowel tissues, etc. Molecular analysis is then performed to confirm whether the biopsy sample of suspect tissue is cancerous or precancerous.

The target of molecular analysis, i.e., DNA, mRNA, DNA methylation, telomorase activity, or mtDNA analysis is selected based on access to instrumentation, qualified analysts, or the nature of the cell sample. The molecular analysis of the cell sample entails a choice among various procedures. Gel electrophoresis, the polymerase chain reaction (PCR) based chemistry, Rolling Circle Amplification (RCA) unimolecular detection system, fluorescence tagging, immunohistochemical staining, mass spectroscopy, and colorimetry are representative examples of effective molecular analysis procedures. The nature of the cell sample, the extraction, and nucleic acid digestion will influence the choice of specific molecular analysis procedure for the optimum analysis.

In the presently preferred embodiment of the invention, the molecular analysis procedure employed is the procedure for identifying microsatellite markers, i.e., repetitive sequences of the DNA, via PCR analysis. It should be understood, however, that the method of the invention may include any reliable molecular analysis technique for determining whether a cell's constituents exhibit a cancerous or wild-type phenotype.

I. Polymerase Chain Reaction (PCR), Commonly Microsatellite Instability (MSI) Testing MSI is identified by electrophoretic resolution of amplified microsatellite DNA sequences. To perform MSI testing, blocks of surgically resected tumor tissue—either a fresh frozen specimen or a formalin-fixed, paraffin-embedded specimen is obtained. The tumor tissue is microdissected to separate neoplastic tissue from normal tissue, and DNA is extracted from both. Samples of genomic DNA from these samples are amplified for a panel of specific mono- and di-nucleotide microsatellite loci using PCR.

PCR products are then analyzed by electrophoresis. Additional bands in the PCR products of the tumor DNA not observed in the normal DNA is scored as instability at that locus (or specific site). According to industry standards, MSI analyses require the use of five MS markers, two mononucleotide repeats and three di-nucleotide repeats. According to the National Cancer Institute's consensus statement on MSI testing, any pair of samples that display instability at two or more of five different loci is scored as high MSI. For details, see Guo, Z., Yamaguchi, K., Sanchez-Cespedes, M., Westra, W. H., Koch, W. M., Sidransky, D., "Allelic Losses in OraTest-directed Biopsies of Patients with Prior Upper Aerodigestive Tract Malignancy", Clinical Cancer Res., 7: 1963-1968, 2001. Further detail to enable one skilled in the art to perform the microsatellite analysis is disclosed in U.S. Pat. No. 6,291,163, to Sidransky, incorporated herein by reference. Automated PCR analysis is described in U.S. Pat. No. 6,326,147, incorporated herein by reference.

II. Gel Electrophoresis

Nucleic acid strands are first selectively digested and then subjected to electrophoresis in which molecules (as proteins and nucleic acids) migrate through a gel (e.g., a polyacrylamide gel) and separate into bands according to size.

III. RCA

Rolling circle amplification (RCA) is a surface-anchored DNA replication reaction that can display single molecular recognition events. RCA successfully visualizes target DNA sequences as small as 50 nts in peripheral blood lymphocytes or in stretched DNA fibers. Signal amplification by RCA can be coupled to nucleic acid hybridization and multicolor fluorescence imaging to detect single nucleotide changes in DNA within a cytological context or in single DNA molecules, enabling direct physical haplotyping and the analysis of somatic mutations on a cell-by-cell basis. Each amplified DNA molecule generated by RCA may be localized and imaged as a discrete fluorescent signal, indicating of a specific molecular ligation event. Expression profiles may be generated as histograms of single molecule counts, as well. The U.S. Pat. Nos. 6,329,150 and 6,210,884 to Lizardi, are incorporated herein by reference to provide ample detail to enable one skilled in the art to practice the disclosed invention employing RCA techniques.

IV. Southern Blotting

Southern blotting can identify differences between normal and mutant alleles and identify genes that are related in other genomes. In a Southern blot, cloned or amplified DNA is digested with a restriction enzyme. The large variety of DNA fragments is separated according to size by electrophoresis and transferred onto a nitrocellulose filter. The fragments are then hybridized with a probe, but only those DNA fragments containing sequences homologous, or identical in base sequence, to the probe are detected. Single-base differences between individuals are detected when that base change creates or destroys a site for the restriction enzyme used to digest the DNA. Deletions or DNA insertions that change the size of the fragment created by the restriction enzyme(s) may also be detected in this manner. U.S. Pat. No. 5,811,2391, incorporated herein by reference, describes a method for single basepair DNA sequence variation detection by Southern blot.

V. Flourescent Tagging

Exact base sequence of a cloned or PCR-amplified DNA fragment is determined by a method called DNA sequencing. DNA sequencing has been automated by using differentially colored fluorescent markers for each of the four DNA bases whereby the fluorescent signal emitted by each of these chromosome "paints" can be read by a sensitive scanner and analyzed by a computer.

VI. DNA Probes

A probe is a stretch of DNA or other nucleic acid that has been tethered to a stable material. The probe is then exposed to a target of free nucleic acid whose identity is being detected (by the probe) through a hybridization reaction (for terminology, see Phimster B: Nat Genet 21 [Suppl]: 1-60, 1999). The probe is generally labeled with a radioactive isotope or a chemical than can be detected after the hybridization takes place. For example, chemiluminescent labels, e.g. 1,2-dioxetanes, alkaline phosphate, or biotin, may be used as hybridization probes to detect nucleotide sequence ladders on membranes generated by the sequencing protocol of Church and Gilbert. See Church, G. M., Gilbert, W., Proc. Natl. Acad. Sci., USA 81, 1991-1995, (1984).

VII. Microarrays

DNA microarrays made of high-speed robotics on inert materials, such as glass or nylon, may be used to identify genes and gene mutations. Preselected probes are exposed to "target" DNA and subsequently analyzed for hybridization patterns using a variety of visualization and information-processing programs and strategies. Identification of genes or gene mutations and the levels of gene expression can be detected and analyzed for many genes simultaneously and more rapidly than by many other techniques.

Various names have been given to these microarrays, such as genome chip, biochip, DNA chip, DNA microarray, gene array, and GeneChip®(registered trademark of "Affymetrix").

WORKING EXAMPLES

The following examples illustrate for those skilled in the art a presently preferred embodiment of the invention and are not intended as a limitation of the scope thereof.

Example I

Location of Suspect Tissue By Mashberg-type Clinical Protocol

Preparation of Clinical Test Solutions

TBO (e.g., the product of Example I of U.S. Pat. No. 6,086,852), raspberry flavoring agent (IFF Raspberry IC563457), sodium acetate trihydrate buffering agent and $H_2O_2$ (30% USP) preservative (See U.S. Pat. No. 5,372,801), are dissolved in purified water (USP), glacial acetic acid and SD 18 ethyl alcohol, to produce a TBO test solution, having the composition indicated in Table A:

TABLE A

| Component | Weight % |
| --- | --- |
| TBO Product | 1.00 |
| Flavor | .20 |
| Buffering Agent | 2.45 |
| Preservative | .41 |
| Acetic Acid | 4.61 |
| Ethyl Alcohol | 7.48 |
| Water | 83.85 |
| | 100.00 |

Pre-rinse and post-rinse test solutions of 1 wt. % acetic acid in purified water, sodium benzoate preservative and raspberry flavor are prepared.

Clinical Protocol

The patient is draped with a bib to protect clothing. Expectoration is expected, so the patient is provided with a 10-oz. cup, which can be disposed of in an infectious waste container or the contents of which can be poured directly into the center of a sink drain, to avoid staining the sink. Environmental surfaces or objects which might be stained are draped or removed from the test area.

A visual oral cancer examination is conducted, without using any instruments which might cause nicks or cuts of soft tissues. Notations are made of the pre-staining appearance of soft tissues and teeth.

The patient rinses the oral cavity with approximately 15 ml. of the pre-rinse solution for approximately 20 seconds and expectorates, to remove excess saliva and provide a consistent oral environment. This step is then repeated with additional pre-rinse solution.

The patient then rinses and gargles with water for 20 seconds and expectorates.

The patient then rinses and gargles with 30 ml. of the TBO test solution for one minute and expectorates.

The patient then rinses with 15 ml. of the post-rinse solution for 20 seconds and expectorates. This step is then repeated.

The patient then rinses and gargles with water for 20 seconds and expectorates. This step is then repeated.

Observations of the oral cavity are then made, using appropriate soft-tissue examination techniques, including retraction, well-balanced lighting and magnification, if necessary. The location, size, morphology, color and surface characteristics of suspect lesions, that have retained blue coloration are made and recorded.

The patient is brought back after 10-14 days for a repeat of the above protocol. This period allows time for healing of any ulcerative or traumatic lesion or irritating etiology that was present at the time of the first examination. A positive stain after the second examination of a suspect area detected in the first examination is considered an indication of cancerous or precancerous tissue.

Early erythroplastic lesions stain blue, often in a stippled or patchy pattern. However, it normal for the stain to be retained by the irregular papiliar crevices on the dorsum of the tongue, which is not a positive indication. Other areas which retain blue stain, but are not regarded as positive include dental plaque, gingival margins of each tooth, diffuse stain of the soft palate because of dye transferred from the retained stain on the dorsum of the tongue, and ulcerative lesions which are easily distinguished. In all instances, however, where a lesion is highly suspect, but does not stain positively with this test, it is nevertheless imperative that a biopsy be taken and subjected to molecular analysis.

Example II

Genetic Alteration Molecular Analysis 58 samples of suspect tissue are obtained from various clinical sites practicing the screening procedure of Example 1. It is determined that genetic alteration analysis of two of these samples is not possible because there is inadequate material on the slides. In the remaining 56 cases neoplastic cells are carefully dissected (in cases with cancer) from normal tissue or epithelium (in all other cases) from normal tissue using a laser capture microdissection scope. This allows isolation of the cells and extraction of DNA for subsequent microsatellite analysis at three critical loci. In cases, there is insufficient DNA and further analysis is not possible. Two of the loci (D9S171 and D9S736) chosen for testing are on chromosomal region 9p21 which contains the p16 gene. A third marker (D3S1067) is located on chromosome 3p21. All molecular studies in the remaining 41 cases are done blinded without knowledge of the pathologic diagnosis.

Within the study, lesions that are stained blue and lesions that are biopsied adjacent to but not within the blue staining areas are separately identified. Thus, in many cases one is able to test both directly the stained areas as well as adjacent nonstained areas. Microsatellite analysis of these critical markers in all of these 41 cases shows the presence of LOH (chromosomal deletions) in virtually all the cases with cancer and carcinoma in situ. In addition, many of the dysplastic lesions and nondysplastic lesions as well as those in the unknown (no pathologic diagnosis) category also harbor clonal genetic changes.

In 12 out of 12 cancer cases a clonal genetic change as expected is identified. In all four cases of carcinoma in situ or severe dysplasia a clonal change is also identified. In 57% of cases of dysplasia (4 out of 7) and 85% of cases without dysplasia (12 out of 14) clonal genetic changes are found in one or more of these markers. In cases with unknown histology clonal genetic changes are identified in 25% (1 of out 4) of the cases. Overall, clonal changes are identified by microsatellite analysis in 80% of the lesions (33 out of 41). This molecular analysis definitively shows that approximately 80% of the lesions identified by the Mashberg-type protocol are clonal.

Having described my invention in such terms as to enable those skilled in the art to understand and practice it, and, having identified the presently preferred embodiments thereof, I claim:

1. A prognostic/diagnostic method for detecting and diagnosing cancerous and precancerous tissue, the method comprising, in combination and in sequence, the steps of:
   (a) topically applying to epithelial tissue a dye that selectively stains cancerous and precancerous tissue to locate suspect tissue, wherein the dye comprises:
      (1) conformational isomers of toluidine blue O, the compounds having the structures

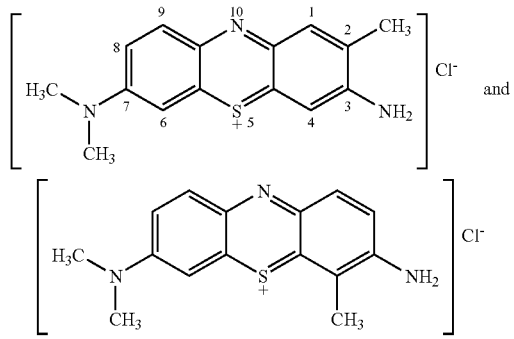

(2) N-demethylation derivatives of the isomers, the compounds having the structures

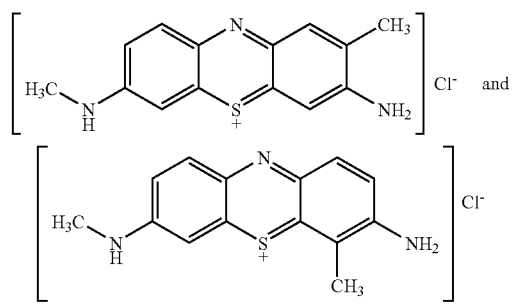

a ratio of combined areas of 254 nm HPLC peaks representing the isomers to combined areas of 254 nm HPLC peaks representing the N-demethylation derivatives being at least about 6:1;
   (b) separating cells from the suspect tissue; and
   (c) subjecting the cells to molecular analysis to determine whether the separated cells exhibit characteristics associated with cell differentiation or cancer.

2. The method of claim 1 wherein step (a) is preceded by saliva test cancer screening to determine whether cancerous or precancerous tissue exists in head and neck tissues and step (b) is then performed on the head and neck tissues.

3. A prognostic/diagnostic method for detecting and diagnosing cancerous and precancerous tissue in a patient's mouth, the method comprising, in combination and in sequence, the steps of:
   (a) conducting a visual examination of the patient's mouth to determine the condition and appearance of soft tissue and teeth in the patient's mouth;
   (b) rinsing the patient's mouth with a solution comprising a staining compound, wherein the staining compound comprises:
      (1) conformational isomers of toluidine blue O, the compounds having the structures

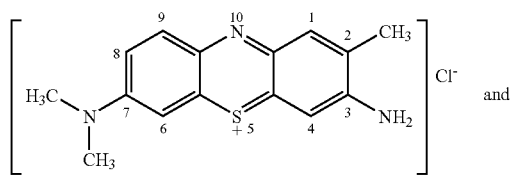

-continued

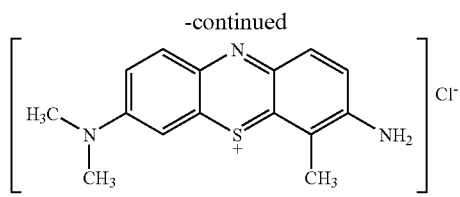

(2) N-demethylation derivatives of the isomers, the compounds having the structures

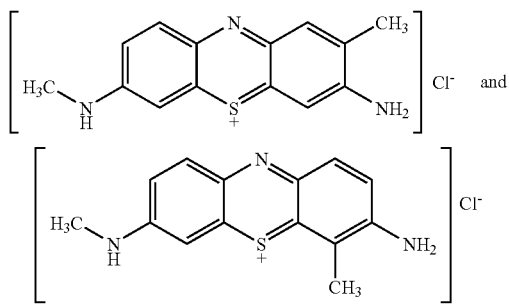

a ratio of combined areas of 254 nm HPLC peaks representing the isomers to combined areas of the peaks representing the N-demethylation derivatives being at least about 6:1;
(c) rinsing the patient's mouth with water;
(d) observing and recording the characteristics of suspect lesions, including their location, size, morphology, color and surface;
(e) removing cells from the suspect lesions;
(f) subjecting the cells to microsatellite analysis to determine loss of heterozygosity (LOH) at critical loci, wherein LOH is indicative of cancer or precancerous cells.

4. The method of claim 3 wherein the visual examination is conducted without using any instruments which might cause nicks or cuts to the soft tissue.

5. The method of claim 3, wherein the critical loci chosen for testing are located in chromosomal regions selected from the group consisting of 9p21 and 3p21.

6. The method of claim 5, wherein the critical loci are selected from any one or a combination of loci selected from the group consisting of D9S171, D9S736, and D3S1067.

7. A prognostic/diagnostic method for detecting and diagnosing cancerous and precancerous tissue, the method comprising, in combination and in sequence, the steps of:
(a) topically applying to epithelial tissue a dye that selectively stains cancerous and precancerous tissue to locate suspect tissue, wherein the dye comprises:
(1) conformational isomers of toluidine blue O, the compounds having the structures

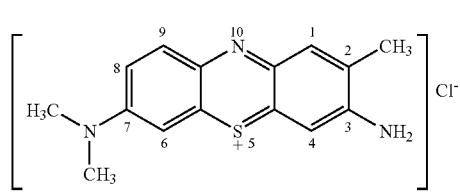

-continued

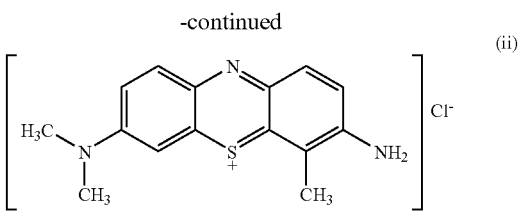

in which the isomer of subparagraph (i) comprises at least 58% of a total organic dye content of the composition,
(b) separating cells from the suspect tissue; and
(c) subjecting the cells to molecular analysis to determine whether the separated cells exhibit characteristics associated with cell differentiation or cancer.

8. The method of claim 7 wherein step (a) is preceded by saliva test cancer screening to determine whether cancerous or precancerous tissue exists in head and neck tissues and step (b) is then performed on the head and neck tissues.

9. The method of claim 7 wherein the visual examination is conducted without using any instruments which might cause nicks or cuts to the soft tissue.

10. A prognostic/diagnostic method for detecting and diagnosing cancerous and precancerous tissue, the method comprising, in combination and in sequence, the steps of:
(a) topically applying to epithelial tissue a dye that selectively stains cancerous and precancerous tissue to locate suspect tissue, wherein the dye is made using a process for manufacturing toluidine blue O, which comprises the steps of
(1) oxidizing N,N-dimethyl-p-phenylene diamine in a first reaction mixture, to form a first intermediate, 2-amino-5-dimethylaminophenyl thiosulfonic acid,
(2) oxidizing the first intermediate and condensing the oxidizate in a second reaction mixture with o-toluidine, forming a second intermediate, indamine thiosulfonic acid,
(3) oxidizing the second intermediate to close the indamine ring thereof, forming a TBO-containing reaction product dissolved in a third reaction mixture,
(4) introducing a complexing reagent into the third reaction mixture, to form a TBO-complex product dissolved in the third reaction mixture,
(5) precipitating the TBO-complex product from the third reaction mixture, and
(6) separating the TBO-complex product, containing conformational isomers of TBO;
wherein the improved process comprises introducing the complexing reagent to a reaction mixture before formation of the third reaction mixture, the complexing reagent being a compound that forms with the N,N-dimethyl-p-phenylenediamine, the first intermediate and/or the second intermediate, a complex that provides steric hinderence to demethylation thereof;
(b) separating cells from the suspect tissue; and
(c) subjecting the cells to molecular analysis to determine whether the separated cells exhibit characteristics associated with cell differentiation or cancer.

11. The method of claim 10 wherein step (a) is preceded by saliva test cancer screening to determine whether cancerous or precancerous tissue exists in head and neck tissues and step (b) is then performed on said head and neck tissues.

* * * * *